United States Patent [19]
Bolnet et al.

[11] Patent Number: 5,342,776
[45] Date of Patent: Aug. 30, 1994

[54] AVIAN HEMOPOIETIC PROGENITOR CELLS

[76] Inventors: Marie C. N. Bolnet, 1021-103 Nicholwood Dr., Raleigh, N.C. 27605; Françoise A. Dieterlen-Lievre, 6 rue de Bellechasse, 75007 Paris, France

[21] Appl. No.: 940,665

[22] Filed: Sep. 4, 1992

[51] Int. Cl.$^5$ .............................................. C12N 5/00
[52] U.S. Cl. ........................... 435/240.2; 435/240.21; 435/240.23; 424/577; 424/582; 424/93.7; 424/93.2; 424/93.21
[58] Field of Search ........... 435/240.2, 240.21, 240.23; 424/93 U, 577, 582, 93 A, 93 B

[56] References Cited

U.S. PATENT DOCUMENTS 5,061,620  10/1991  Tsukamoto et al.

OTHER PUBLICATIONS

Leblanc, J. Neurobiology 21(4): 567–577 (1990).
Wolff et al., Texas Rep. Biol. Med. 10: 463–472 (1952).
C. Nicolas-Bolnet et al., *Experimental Cell Research* 196, 294–301 (1991).
F. Dieterlen-Lievre et al., *Development* The Avian Model in Developmental Biology; From Organism to Genes, Editions du CNRS–(1990).
Francoise Cormier, et al., *Experimental Cell Research* 190, 113–117 (1990).
Luc Pardanaud, et al., *Development* 105, 473–485 (1989).
Francoise Cormier et al., *Development* 102, 279–285 (1988).
Francoise Cormier et al., *Development* 118, 167–175 (1986).

*Primary Examiner*—Jasemine C. Chambers
*Attorney, Agent, or Firm*—Bell, Seltzer, Park & Gibson

[57] ABSTRACT

Avian hemopoietic progenitor cells of an earlier ontogenic stage than heretofore obtained are disclosed. The cells are produced by culturing suitable cells in a media containing avian embryo extract. Chicken hemopoietic progenitor cells and chicken embryo extract are preferred. Also disclosed are veterinary pharmaceutical formulations comprised of the earlier stage hemopoietic progenitor cells.

20 Claims, 3 Drawing Sheets

AVIAN HEMOPOIETIC PROGENITOR CELLS

FIELD OF THE INVENTION

The present invention relates to the amplification of early-stage arian hemopoietic progenitor cells and a cell culture system employing avian embryo extract for producing the same.

BACKGROUND OF THE INVENTION

Blood cells are divided into several distinct cell lines, including the erythroid cell line, the lymphoid cell line, and the myeloid cell line. Each line may include several different blood cell types, with (for example) the myeloid cell line including monocytes and granulocytes.

It has been demonstrated that the various blood cells descend from a single ancestor cell type, termed the hemopoietic stem cell. These stem cells differentiate into various distinct progenitor cells, and the progenitor cells in turn differentiate into the various types of mature cells found in blood. The various cell types involved in this system have been well studied in mouse and man: for example, a human hemopoietic stem cell is disclosed in U.S. Pat. No. 5,061,620 to Tsukamoto et al. Much less attention has been devoted to the study of avian species. See generally F. Dieterlen-Liévre et al., in *The Avian Model in Developmental Biology: From Organism to Genes* (Editions du CNRS 1990).

F. Cormier and F. Dieterlen-Liévre, *Development* 102, 279-285 (1988) shows that the wall of the chick embryo aorta harbors monocytic colony-forming cells, granulocytic colony-forming cells, granulocytic/monocytic colony-forming cells, and burst-forming erythroid units. The cells were isolated in a semi-solid (i.e., gelified) cell culture. Earlier hemopoietic progenitor cells were not isolated. See also F. Cormier et al., *Developmental Biology* 118, 167-175 (1986).

F. Cormier and F. Dieterlen-Liévre, *Exp. Cell Res.* 190, 113-117 (1990), describes long-term cultures of chicken hemopoietic bone marrow cells which establish a stromal layer and produce clonable precursors.

C. Nicolas-Bolnet et al., *Exp. Cell Res.* 196, 294-301 (1991), describes the developmental kinetics of monocytic colony-forming cells, granulocytic colony-forming cells, and granulocytic/monocytic colony-forming cells from the avian embryo spleen. This also employed a gelified cell culture. It was noted that no erythroid or multipotent progenitor cells could be developed in the culture system described. With the growth activities used, the colonies reach final maturation within three days.

SUMMARY OF THE INVENTION

We have found that avian embryo extract (e.g., chicken embryo extract (CEE)), when incorporated into avian hemopoietic cell cultures, enables the isolation and multiplication of sustained earlier-stage hemopoietic progenitor cells than heretofore isolated.

In view of the foregoing, a first aspect of the present invention is a method of culturing avian hemopoietic cells in a culture media (preferably a semi-solid culture media), wherein avian embryo extract is included in said culture media so that hemopoietic progenitor cells of an earlier ontogenic stage are obtained than those hemopoietic progenitor cells obtained when avian embryo extract is not included in said culture media. The earlier-stage hemopoietic cells obtained are (a) intensely basophilic after May-Grünwald-Giemsa staining; and (b) essentially free of hemopoietic differentiation markers for granulocytic colony-forming cells (G-CFC), monocytic colony-forming cells (M-CGC), and granulocytic/monocytic colony-forming cells (GM-CFC) after May-Grünwald-Giemsa staining. In one embodiment, the earlier stage hemopoietic cells are larger in size than G-CFC, M-CGC, or GM-CFC descended from a cell of said avian embryonic hemopoietic organ tissue.

A second aspect of the present invention is a cell culture comprising isolated early avian hemopoietic progenitor cells, wherein the progenitor cells are (a) descended from an avian embryonic hemopoietic organ tissue cell; (b) intensely basophilic after May-Grünwald-Giemsa staining; and (c) essentially free of hemopoietic differentiation markers for G-CFC, M-CGC, and GM-CFC after May-Grünwald-Giemsa staining.

A third aspect of the present invention is an isolated early avian hemopoietic progenitor cell, which cell is descended from an avian embryonic hemopoietic organ tissue cell, intensely basophilic after May-Grünwald-Giemsa staining, and essentially free of hemopoietic differentiation markers for G-CFC, M-CGC, and GM-CFC after May-Grünwald-Giemsa staining.

A fourth aspect of the present invention is a pharmaceutical formulation comprising early avian hemopoietic progenitor cells, wherein said progenitor cells are (a) descended from an arian embryonic hemopoietic organ tissue cell; (b) intensely basophilic after May-Grünwald-Giemsa staining; and (c) essentially free of hemopoietic differentiation markers for G-CFC, M-CGC, and GM-CFC after May-Grünwald-Giemsa staining.

The foregoing and other objects and aspects of the present invention are explained in detail in the drawings provided herein and the specification set forth below.

DETAILED DESCRIPTION OF THE INVENTION

Figure 1:
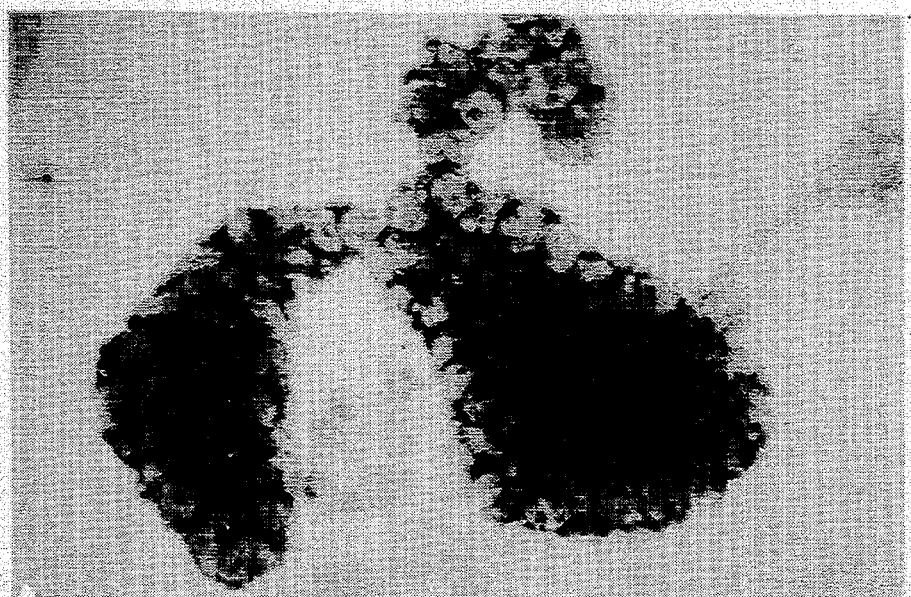
FIG. 1 is a photograph of cells of the present invention after May-Grünwald-Giemsa staining.

The term "avian", as used herein, refers to any arian species, including but not limited to chicken, turkey, duck, goose, quail and pheasant. Chicken is currently preferred.

The term "sustained", as used herein with respect to cells and cell cultures, refers to a cell or cell culture capable of undergoing further cell division, even if the cells are eventually subject to senescence.

The term "semi-solid" refers to a gelified growth media, i.e., a media in which movement of cells in the media as they grow is restrained so that cells grow as discrete, separate colonies of like cells therein.

The stage of development of avian embryos from which cells are obtained for carrying out the present invention will depend on the particular source of the cells. For example, cells from the aortic region are obtained from about 3.5 to 4 day chicken embryos (with day referring to day of incubation of the embryo in ovo), spleen cells are obtained from about 14 to 16 day chicken embryos, and bone marrow cells are obtained from about 16 to 21 day chicken embryos. Such cells from other avian species are obtained from embryos at essentially the same stage of embryonic development as the stage corresponding to the day of incubation given for chicken embryos herein (which may occur at a different day of incubation than for chicken).

The media used in carrying out the present invention may be any suitable media as conventionally used in the culture of avian hemopoietic cells. In general, such media will be an aqueous media in liquid or semi-solid form. Semi-solid media may be produced by including agar, methyl-cellulose, collagen, plasma clot or the like in the media. The media itself will typically contain a source of essential amino acids such as bovine serum albumin, essential lipids and vitamins, cholesterol, linoleic acid, cholesterol, and antibiotics. Preferably the media also includes iron-saturated transferrin. Liquid media may be periodically replenished in cell cultures grown in liquid media by removing a portion of the liquid media and replacing that portion with fresh media, in accordance with known techniques. Cells of the present invention remain capable of continued growth after two, three, and even four weeks of culture in liquid media.

In one embodiment, the growth media is a semi-solid media, as this allows the growth of discrete colonies of cells consisting essentially of cells of the present invention and separation of these cells from others. Once cells of the present invention are obtained through the isolation of colonies thereof in semi-solid media these cells can then be transferred to a liquid media and expanded therein. Cells expanded in liquid media can then be used for the production of pharmaceutical formulations of such cells as explained below.

As noted above, it is important that the media contain avian embryo extract. The preparation of avian embryo extract is known. First described in connection with the pioneering studies of Strangeways and Fell (see T. Strangeways and H. Fell, *Proc. Royal Soc. London B* 99, 340–364 (1926), T. Strangeways and H. Fell, *Proc. Royal Soc. London B* 100, 273–283 (1927)), chicken embryo extract (CEE) is also known as a major component of organ culture media and its preparation is known in connection with the preparation of such media. See E. Wolff and K. Haffen, *Texas Rep. Biol. Med.* 10, 463–472 (1952). CEE is currently used to culture embryonic neural cells, but has not heretofore been applied to hemopoietic cells, and has not been proposed as a means for obtaining early avian hemopoietic progenitor cells. Avian embryo extract from avian species other than chicken is prepared in like manner to chicken embryo extract. Embryos used for the preparation of avian embryo extract are typically at embryonic stage 35 or 36 (for chicken, day 9 or 10 of in ovo incubation), and more preferably stage 36 (for chicken, day 10 of in ovo incubation).

Cell cultures of the present invention may be prepared as veterinary pharmaceutical preparations for administration to birds by (if necessary) dissociating the cells (e.g., by mechanical dissociation) and intimately admixing the cells with a pharmaceutically acceptable carrier, preferably an aqueous pharmaceutically acceptable carrier such as a growth media which is pharmaceutically acceptable for injection into a bird embryo or a pyrogen-free saline solution (e.g., a phosphate-buffered pyrogen-free saline solution). In the alternative, the cells may be cryopreserved or lyophilized in accordance with known techniques (see, e.g., W. Boyce et al., *Preservation of Fetal and Neonatal Hematopoietic Stem and Progenitor Cells of the Blood,* U.S. Pat. No. 5,004,681, the disclosure of which is to be incorporated herein by reference) for subsequent reconstitution as a pharmaceutical formulation and administration to birds. Pharmaceutical preparations of such cells, whether or not they include a pharmaceutically acceptable carrier, are generally contained in a sterile container, such as a glass vial for injection. Avian hemopoietic progenitor cells in such preparations may be transformed so as to carry a heterologous DNA sequence into an avian subject, in the manner described in greater detail below.

Hemopoietic progenitor cells of the present invention and veterinary pharmaceutical formulations containing the same are useful, among other things, as a tool for the study of embryological development (i.e., by labelling the cells with a marker gene such as a gene encoding β-galactosidase and observing their distribution after injection in vivo) and for the production of somatic transgenic poultry. They are useful in allowing the application of homologous recombination to the production of transgenic poultry.

The present invention provides a new method of altering the phenotype of a bird and the birds so produced with the avian hemopoietic progenitor cells disclosed herein. The method comprises transfecting avian hemopoietic progenitor cells as disclosed herein with the DNA sequence in vitro (e.g., by electroporation or transformation with a retroviral vector), and then injecting the transfected hemopoietic progenitor cells into an egg containing an embryonic bird. For example, progenitor cells may be injected into the coelom of the embryo at a time when hemopoietic progenitor cells are capable of surviving therein (e.g., at day 3 of incubation for chickens). In another example, progenitor cells may be injected into the yolk sac (e.g., into a blood vessel) or onto the chorioallantoic membrane, preferably into the subgerminal cavity, and preferably during early embryonic development (e.g., prior to day 2 or 3 of incubation, and most preferably prior to day 1 of incubation). In either case treatment is carried out with the DNA sequence being effective to cause a change in phenotype in the bird after hatch (e.g., a change in growth rate, feed efficiency, disease resistance, or a combination of all of these factors). Preferably, the egg into which the DNA is introduced is incubated to hatch, and the bird so produced raised to at least an age at which the change in phenotype is expressed. It is of no deleterious consequence if the transformed embryo and bird is chimeric, so long as a physiological response is achieved in the animal after hatch sufficient to evoke the phenotypic change sought.

The mechanism of in ovo injection is not critical, but it is preferred that the method not unduly damage the tissues and organs of the embryo or the extraembryonic membranes surrounding it so that the treatment will not decrease hatch rate. A hypodermic syringe fitted with a needle of about 18 to 26 gauge is suitable for the purpose. Depending on the precise stage of development and position of the embryo, a one-inch needle will terminate either in the fluid above the chick or in the chick itself. A pilot hole may be punched or drilled through the shell prior to insertion of the needle to prevent damaging or dulling of the needle. If desired, the egg can be sealed with a substantially bacteria-impermeable sealing material such as wax or the like to prevent subsequent entry of undesirable bacteria. It is envisioned that a high speed automated injection system for avian embryos will be particularly suitable for practicing the present invention. Numerous such devices are available, exemplary being the EMBREX INOVOJECT ™ system (described in U.S. Pat. Nos. 4,681,063 and 4,903,625 to Hebrank), and U.S. Pat. Nos. 4,040,388, 4,469,047, and 4,593,646 to Miller. The disclosure of these references and all other patent references cited herein are to be incorporated herein by reference. All such devices, as adapted for practicing the present invention, comprise an injector containing the hemopoietic progenitor cells as described herein, with the injector positioned to inject an egg carried by the apparatus with the DNA. In addition, a sealing apparatus operatively associated with the injection apparatus may be provided for sealing the hole in the egg after injection thereof.

The DNA sequence introduced in ovo with hemopoietic progenitor cells of the invention is, in general, a construct comprised of a promoter functional in avian cells and a gene encoding a peptide or protein operably linked to the promoter. Preferably, the protein or peptide is physiologically active and capable of producing a phenotypic change in the bird. In general, the DNA construct may be a linear DNA sequence (introduced into the hemopoietic progenitor cells of the invention by electroporation) or a sequence carried by a vector or other suitable carrier for transforming the hemopoietic progenitor cells of the invention, such as liposomes, calcium phosphate, or DMSO. Vectors, as discussed below, may be plasmids, viruses (including retroviruses), and phage, whether in native form or derivatives thereof.

Illustrative of genes encoding a protein or peptide are those which encode a protein or peptide selected from the group consisting of growth hormone, thyroid releasing hormone (TRH), Marek's MDX, and immunogenic recombinant antigens such as that for coccidiosis.

The production of cloned genes, recombinant DNA, vectors, transformed host cells, proteins and protein fragments by genetic engineering is well known. See e.g., U.S. Pat. No. 4,761,371 to Bell et al. at Col. 6 line 3 to Col 9 line 65; U.S. Pat. No. 4,877,729 to Clark et al. at Col. 4 line 38 to Col 7 line 6; U.S. Pat. No. 4,912,038 to Schilling at Col. 3 line 26 to Col. 14 line 12. Protocols for restriction endonuclease digestion, preparation of vectors, DNA purification and other such procedures were essentially as described in standard cloning manuals. See Sambrook et al., *Molecular Cloning, a Laboratory Manual,* (2d Ed., Cold Spring Harbor Press, New York (1989)).

A vector is a replicable DNA construct used herein to either amplify and/or express DNA encoding the gene of interest. A suitable expression vector will have controlling elements capable of expressing the cloned cDNA or genomic DNA placed in the correct orientation when the vector is introduced into the correct host. Such elements typically include but are not limited to a promoter region which interacts specifically with cellular proteins involved in transcription, enhancer elements which can stimulate transcription many-fold from linked heterologous promoters, a splice acceptor and/or donor sequences, and termination and polyadenylation signals. Also required is the sequence for a ribosome binding site capable of permitting translation which is operably linked to the gene to be expressed. Recently, a muscle-specific promoter has been isolated which is positioned upstream of both the skeletal muscle structural gene and the essential proximal promoter element and is operably associated with each. (Mar and Ordahl, *Proc. Natl. Acad. Sci.* USA 85, 6404–6408 (1988)). Vectors comprise plasmids, viruses (e.g. adenovirus, cytomegalovirus), phage, and DNA fragments integratable into the host genome by recombination. The vector replicates and functions independently of the host genome, or may in some instances integrate into the genome itself.

The present invention is explained in greater detail in the following non-limiting Examples, in which $\mu g$ means micrograms, ml means milliliters, mM means milliMolar, M means Molar, IU means International Units, G means gravity, and temperatures are given in degrees Centigrade.

EXAMPLE 1

Tissue and Cell Preparation

Fertile chicken eggs (white Leghorn) were obtained from a commercial source and hatched in accordance with standard techniques.

Bone marrow cells from tibias and femurs of embryonic day 16 chick embryos (E16), embryonic day 21 chick embryos (E21), and day one post hatch chicks (P1) were flushed using a syringe containing Dulbecco Modified Eagle's medium (DMEM, Gibco). After mechanical dissociation of the cell aggregates with a pipette, the suspension was filtered over a nylon gauze and centrifuged at 1000 revolutions per minute (rpm) for 10 minutes. The cells were counted using the trypan blue dye exclusion test in accordance with known techniques.

Spleens from 10 to 20 embryos (E16) were dissected out under sterile condition and gently teased apart between two glass microscope slides in DMEM. The resulting suspension was then treated as described above.

Truncal aortae from 120 E4 embryos were dissected out under sterile conditions, dissociated with collagenase (0.1%) in phosphate buffered saline (PBS) without calcium or magnesium, and incubated for 15–20 minutes at 37° C. After rapid dissociation by pipetting and addition of foetal calf serum (FCS, Intermed) to stop the action of the enzyme, the cell suspension was created as described above.

EXAMPLE 2

Growth Factor Preparation

Fibroblast conditioned medium (FCM) FCM used as source of growth activities was prepared in accordance with known techniques, comprising to Dodge and Moscovici's procedure (see W. Dodge and C. Moscovici, *J. Cell. Physiol.* 81, 371–386 (1973)) modified as described in C. Nicolas-Bolnet et al., supra. FCM was used at concentration of 3%.

Chick embryo extract (CEE) was also prepared in accordance with known techniques. See E. Wolff and K. Haffen, *Texas Rep. Biol. Med.* 10, 463–472 (1952). In overview, 10 to 20 chick embryos were dissected out in PBS under sterile conditions. The embryos were rinsed 3 times in PBS before homogenization through a 50 cc syringe (carried out by removing the plunger, placing the embryo in the body of the syringe, inserting the plunger back into the syringe and forcing the embryo through the syringe opening). The homogenate was diluted in DMEM at a 1:1 volume:volume ration and centrifuged at 10,000 rpm's (approximately $11,950 \times G$) for 15 minutes at 0° C. The supernatant (the CEE) was frozen prior to use and otherwise kept at 20° C. After thawing, the supernatant was filtered on 0.45 micron filter paper and used as described below, at a concentration of 10% in the final media.

EXAMPLE 3

Plasma Clot Culture Preparation

Plasma clot cultures were prepared with bone marrow, spleen, and aortae cells. Cultures were performed in duplicate at 37° C. or 40° C. in a humidified atmosphere with 5% $CO_2$ in air.

The serum-free medium (basic medium) is a modified version of media for mammalian cells developed by F. Cormier and F. Dieterlen-Liévre, *Development* 102, 279–285 (1988). See C. Nicolas-Bolnet et al., supra. The media consists of: bovine serum albumin (25 mg/ml, Boehringer-Mannheim), soy-bean lipids (20 µg/ml Boehringer-Mannheim), iron-saturated transferrin (30 µg/ml, Boehringer-Mannheim), linoleic acid (5.6 µg/ml, Sigma), cholesterol (7.8 µg/ml, Prolabo) (with these two last components being prepared together as described by Stewart et al., *Exp. Hematol.* 12, 309–318 (1984)), α-thioglycerol ($10^4$M, Calbiochem), Basal Medium Eagle (BME) vitamins solution (1%, GIBCO), glutamine (2 mM, GIBCO), penicillin (100 IU/ml GIBCO), and steptomycin (100 µg/ml, GIBCO). This basic medium was supplemented with citrated bovine plasma (10% GIBCO) and clotted by the addition of thrombin (1 IU/ml; Produits Roche, France). Chick embryo extracts (CEE) or Fibroblast Conditioned Medium (FCM) were added as indicated below. Cells ($25 \times 10^3$) were seeded and cultured for 3 to 8 days. Morphological and quantitative analysis were performed in accordance with known techniques. See C. Nicolas-Bolnet et al., supra.

EXAMPLE 4

Liquid Culture Preparation

Liquid cultures were prepared with bone marrow cells. Cultures were again performed in duplicate at 37° C. or 40° C. in a humidified atmosphere with 5% $CO_2$ in air.

The basic medium is the same as the media described for the plasma clot culture in Example 2 above. $13 \times 10^6$ cells were seeded in 10 ml, of an α-medium (GIBCO) supplemented with basic serum-free medium as described above. Three cultures were initiated: one in medium supplemented with CEE, one in media supplemented with FCM, and one in media containing neither CEE nor FCM as a control. Those cultures were incubated at 37° C. The cultures lasted 3 to 32 days. Every two or five days, half of the supernatant was removed and the same volume of fresh medium was added to the initial dish. The removed supernatant was centrifuged at 1,000 rpm for 10 minutes and the number of cells in the pellet was evaluated. The cells from the pellet were cultured in α-medium containing 5 ml of fresh medium plus 5 ml of the centrifuged supernatant.

The supernatant cells were analyzed morphologically on smears stained according to the May-Grünwald-Giemsa procedure. These cells were also tested for their colony-forming capacity in plasma clot culture supplemented with FCM or CEE.

EXAMPLES 5–6

Culture of Hemopoietic Progenitor cells in Liquid and Semi-Solid Media Containing Chicken Embryo Extract The effects of CEE added to a basic serum-free medium on chicken hemopoietic progenitor cells were tested in two different culture systems: the semi-solid plasma clot system and the liquid culture system. The semi-solid plasma clot system was used to enumerate colonies the nature of which could be diagnosed on May-Grünwald-Giemsa stained preparations. In this system, colonies were evaluated after 3 and 8 days of culture. The liquid culture system was used to determine how long the cells would survive and multiply, while their potentialities were tested after the liquid culture period in the semi-solid assay.

We have previously analyzed the potentialities of cells in the bone marrow, the spleen, and the aortic region of chicken embryos at different stages of ontogeny using the semi-solid media then available: i.e. they contained either chicken serum or FCM as growth activity sources. These sources yielded, in these two types of media, only late progenitors (M-CFC in the presence of chicken serum; M-CFC, G-CFC and GM CFC in the presence of FCM and a very low titer of serum). The unipotent or bipotent colonies derived from these progenitors differentiated within three days of culture and died. No major difference can be ascribed to one of these hemopoietic organs or site.

To follow how hemopoietic cells fare in the presence of CEE, two different temperatures were use. 37° C. is considered the optimal temperature for the differentiation of BFU-E and CFU-E. See J. Samarut and M. Bouabdelli, *J. Cell. Physiol.* 105, 553–563 (1981). In contrast, 40° C. is nearer to the internal temperature of birds and is favorable for the differentiation of macrophages and granulocytes colonies. On the whole, the colonies became large and well differentiated at 37° C. They appear to differentiate much more rapidly at 40° C.

The diagnosis of colony types relied on their morphological appearance and the presence of differentiation markers after May-Grünwald-Giemsa staining carried out in accordance with techniques known or readily available to those skilled in the art. See M. Gabe, *Techniques histologiques.* Masson et Cie (1968). May-Grünwald-Giemsa staining visualizes cytoplasmic and nuclear features of the stained cells. The procedure is, in overview, carried out as follows: cells (affixed to microscope slides) are covered (e.g., 5 drops) with May-Grünwald stain and allowed to sit for 3 minutes; cells are then covered with essentially the same volume of either distilled water or phosphate buffer at pH 7.2 (the phosphate buffer comprised of 9.1 grams of $KH_2PO_4$ and 9.4 grams of $Na_2HPO_4$ in 1 liter of distilled water) and allowed to sit for 3 minutes; cells are then rapidly washed with distilled water, covered with diluted Giemsa stain (1 ml Giemsa stain:20 ml distilled water) and allowed to sit for 20 minutes; cells are then rinsed thoroughly, allowed to air dry, and mounted with a suitable mount such as Permmount or Canadian balsam.

Figure 2:
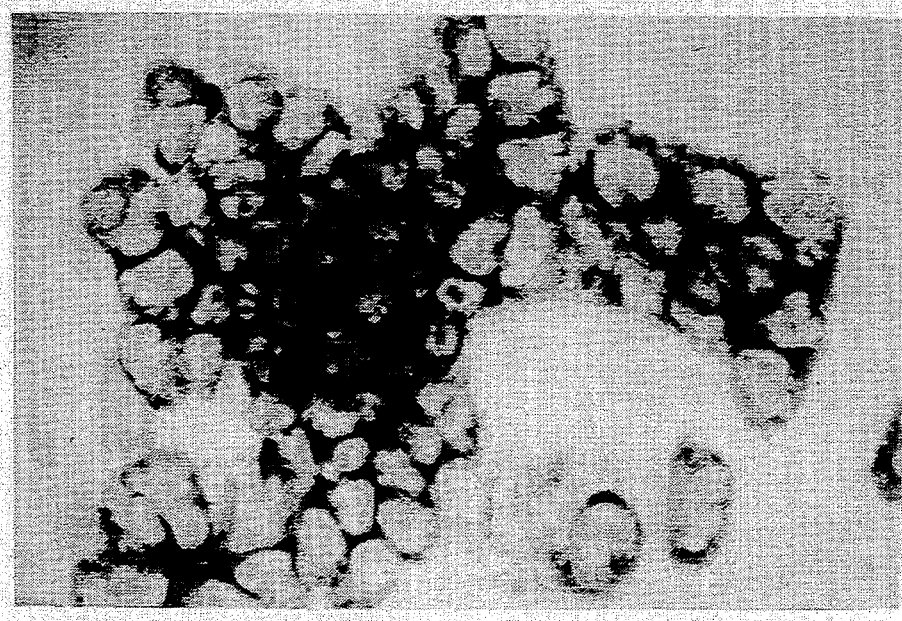
FIG. 2 is a photograph of cells of the present invention after May-Grünwald-Giemsa staining. Note that these cells appear larger in size than G-CFC, M-CGC, or GM-CFC descended from a cell of arian embryonic hemopoietic organ tissue.

The hemopoietic differentiation markers for granulocytic colony-forming cells (G-CFC), monocytic colony-forming cells (M-CGC), and granulocytic/monocytic colony-forming cells (GM-CFC) after May-Grünwald-Giemsa staining are the presence of cytoplasmic granules and/or vacuoles. With these differentiation markers it was possible to distinguish several different colony types. All colony types could reach a size of 100 to 200 cells and were composed of tightly set cells. Some colonies, not heretofore observed, were estimated as the most immature because of the absence of differentiation markers (i.e., were essentially free of cytoplasmic granules and cytoplasmic vacuoles). The newly observed cells of these colonies were intensely basophilic. Two different types of the novel cells of these colonies could be distinguished by the size of the cells (FIGS. 1 and 2). Colonies with larger cells are, in our view, the ontogenically earlier. It is impossible to conclusively diagnose from their initial appearance alone whether these colonies are committed towards one particular lineage or another. In some cases, scarce peripheral cells in the colonies exhibit purple granules, indicating their bias towards the granuloid lineage. In other cases, cells of the colonies become smaller, more compact and slightly elongated, indicating their bias toward the erythroid lineage.

Figure 3:
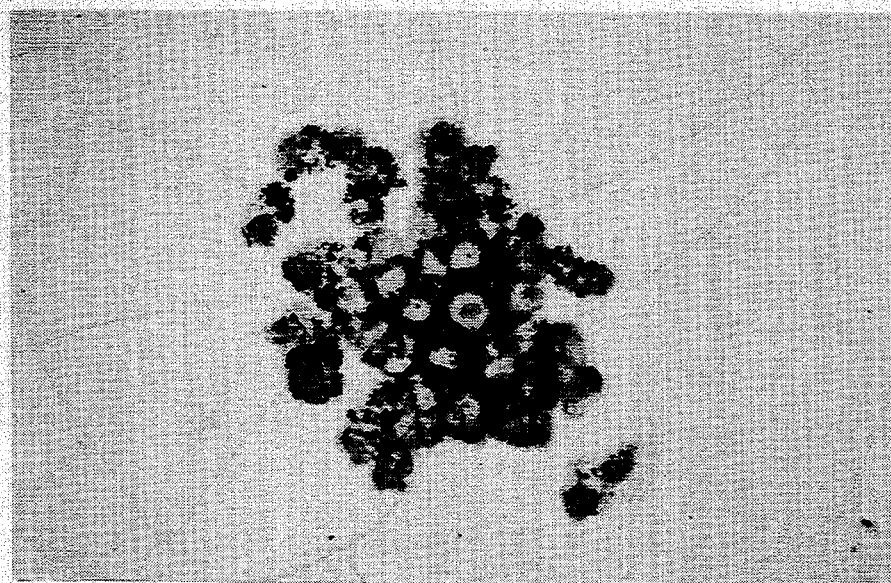
FIG. 3 is a photograph of cells which appear similar to cells described in the prior art after May-Grünwald-Giemsa staining.
Figure 4:
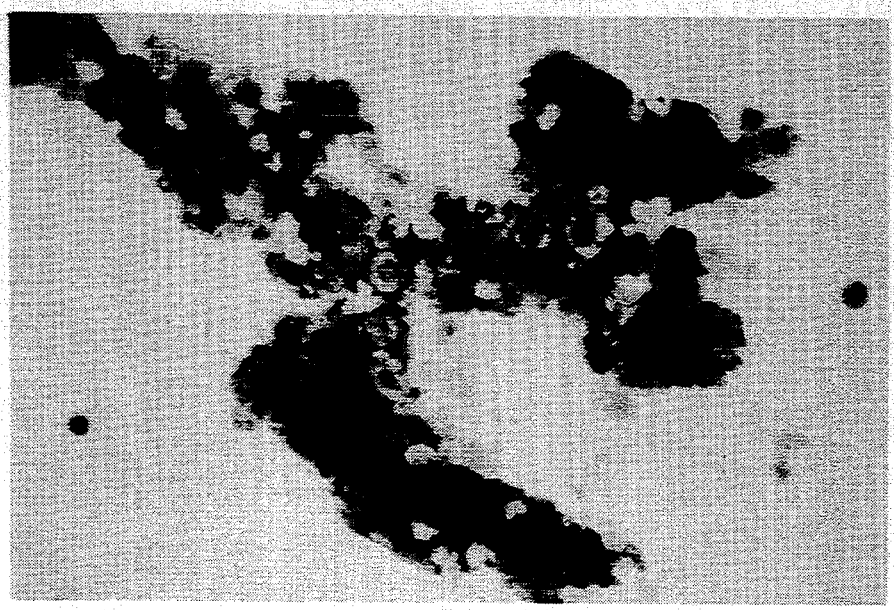
FIG. 4 is a photograph of cells which appear similar to cells described in the prior art after May-Grünwald-Giemsa staining.

In addition to the novel colonies observed, some colonies are readily identified (FIGS. 3 and 4), either as granuloid, (most of their cells contain granules) or as erythroid (they all display the signs of degeneration that affect immature erythroid cells in this system, since erythropoietin is missing and they cannot pursue their evolution).

Cultures in semi-solid media. E16 bone marrow and E4 aortae cells gave similar results at 37° C. after 3 days of culture (Table 1). The more numerous colonies were the differentiated ones (granulocytes, erythroblasts, or mixed colonies). Undifferentiated ("blast") colonies displayed the same frequency in both cases. In cultures of bone marrow cells they appeared slightly more advanced, from the indented aspect of the cell nuclei.

The E16 spleen gave different results. No true colonies developed, but very numerous small clusters, made of 8 to 16 cells, with or without granules.

TABLE 1

Number of colonies developing in plasma clot cultures after 3 days at 37° C. for 25 × 10³ seeded cells.

| COLONY TYPE | AORTA (E4) | BONE MARROW (E16) |
|---|---|---|
| blasts | 40.5 + 13 | 41 + 7.20 |
| Macrophages (Ma) | 0 | 7 + 0.4 |
| Granulocytes (Gr) | 93.5 + 21 | 104.66 + 4.04 |
| Erythroblasts (Eb) | 104 + 14 | 66.33 + 17.28 |
| Gr-Eb | 1 + 1 | 16.66 + 1.66 |
| Gr-Ma-Eb | 0 | 0 |
| Gr-Ma | 0 | 2.33 + 0 |
| Thrombocytes | 5 + 7 | 0.33 + 0 |
| Total | 244 + 9 | 238.31 + 9.20 |
| n | 3 | 4 | n = number of experiments, each in duplicate.

At 40° C. in the case of bone marrow and aorta, the assortment of colonies was reduced to the more differentiated ones, mostly granulocytic in the case of bone marrow and granulocytic and erythroid in the case of aorta cells. On the other hand, this temperature appeared more favorable for spleen cells that gave rise to large granuloid colonies within 3 days (Table 2).

When cultures were maintained for 8 days, differences appeared between results obtained with different cell preparations. No colonies survived in aorta cell cultures. In the case of both spleen and bone marrow, the number of colonies was drastically reduced, i.e. only 10 or 12 colonies were observed instead of around 200 at day 3. Out of these 10 to 12, most colonies resembled the ones found at the earlier date. Three or four, however, belonged to the novel colony type noted above (FIG. 2): colony size was extremely large (more than 200 cells), and cell size was also larger. We interpret these colonies as the progeny of very early progenitors which begin their evolution somewhat later during the culture course.

TABLE 2

Number of colonies developing in plasma clot cultures at 40° C. after 3 days.

| COLONY TYPE | AORTA (E4) | BONE MARROW (E16) | SPLEEN (E16) |
|---|---|---|---|
| Blasts | 0.25 + 0.5 | 4.5 + 3 | 0 |
| Macrophages | 0 | 4.5 + 3 | 0 |
| Granulocytes | 32 + 10 | 208 + 25 | 201 + 12 |
| Erythroblasts | 80.75 + 17 | 0 | 61 + 8 |
| Gr-Eb | 3.5 + 2 | 0 | 0 |
| Gr-Ma-Eb | 0 | 0 | 0 |
| Gr-Ma | 0 | 0 | 0 |
| Thrombocytes | 0.5 + 0.8 | 0 | 0 |
| Total | 177 + 22 | 213 + 15 | 262 + 31 |
| n | 3 | 4 | 4 |

At 40° C., cultures maintained for 8 days had a very poor appearance. Colonies were very scarce, they were of the granulocyte type. Cultures tended to be invaded by fibroblasts.

Cultures in liquid medium. This type of culture was undertaken in order to define whether long term maintenance of early progenitors could be obtained and whether these progenitors could be retrieved and reseeded in semi solid media containing either CEE or FCM (differentiation medium), giving rise again to colonies. The cells tested in this system were E21 and E16 bone marrow.

Figure 5:
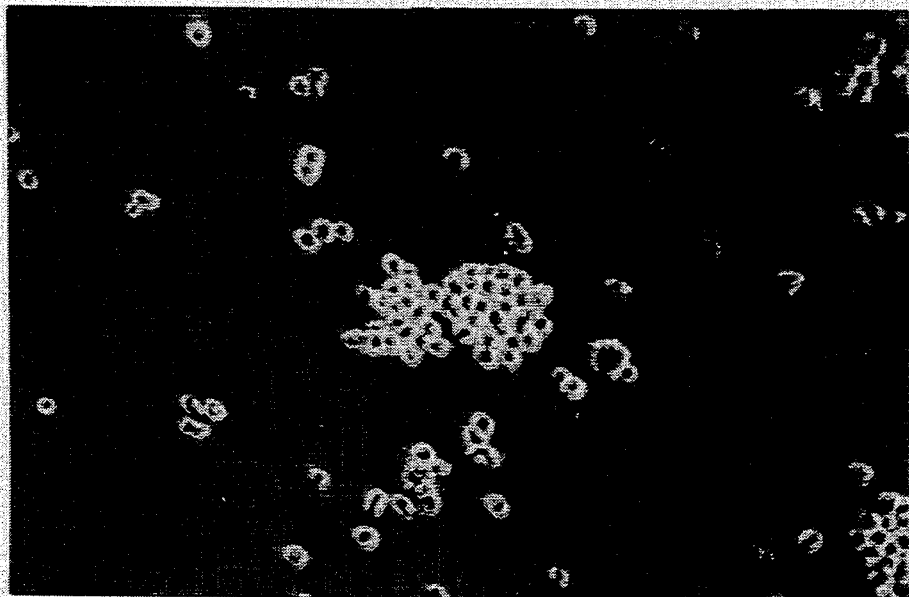
FIG. 5 is a photograph of cells of the present invention which have been expanded in liquid culture viewed under phase contrast.
Figure 6:
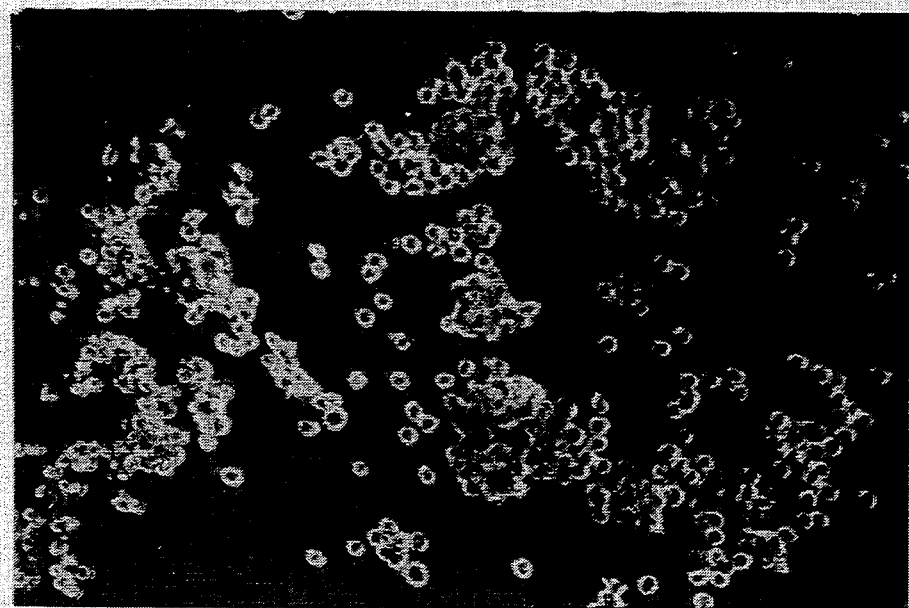
FIG. 6 is a photograph of cells of the present invention which have been expanded in liquid culture viewed under phase contrast.

Expansion of bone marrow cells in this system was enormous (Table 3) at least until day 15. It was essential to change half of the medium every 4 days, the cells in the eliminated medium being then either receded in semi-solid medium to test their colony forming capacity, or being submitted to morphological analysis. At all stages these cells were round shaped and mostly devoid of differentiation markers. Some displayed a few granules. The cells that were replenished with new medium were lightly adhering, forming aggregates that grew with time (FIGS. 5 and 6). Three series (with three dishes in each) were maintained for 32 days. Cells with many granules became more numerous by then. However, cultures could probably be maintained longer. Without either CEE or FCM, cells began dying immediately and all had disappeared by day 8. With FCM all cells were dead by day 10.

TABLE 3

Cell Kinetics in liquid culture medium.

| DAYS | CEE | FCM | CONTROL |
|---|---|---|---|
| 0 | 13 × 10⁶ cells in 10 ml | 13 × 10⁶ cells in 10 ml | 13 × 10⁶ cells in 10 ml |
| 4 | 24 × 10⁶ | 30 × 4 × 10⁶ | 1.8 × 10⁶ |
| 8 | 23 × 10⁶ | 4.2 × 10⁶ | 0 |

TABLE 3-continued

| | Cell Kinetics in liquid culture medium. | | |
|---|---|---|---|
| DAYS | CEE | FCM | CONTROL |
| 10 | $35 \times 10^6$ | 0 | 0 |
| 15 | $46 \times 10^6$ | 0 | 0 |
| 20 | $20 \times 10^6$ | 0 | 0 |
| 28 | $4.2 \times 10^6$ | 0 | 0 |
| 32 | $2 \times 10^6$ | 0 | 0 |

These data indicate that avian embryo extracts such as chicken embryo extract, a nutrient solution that has previously proved efficient in permitting the growth and differentiation of organ rudiments retaining their tridimensional structure and tissue interactions, and that are also favorable for the in vitro survival and differentiation of neuronal or glial precursors, permit the survival and multiplication of hemopoietic progenitor cells of an earlier ontogenic stage than heretofore obtained.

The foregoing examples are illustrative of the present invention, and are not to be construed as limiting thereof. The invention is defined by the following claims, with equivalents of the claims to be included therein.

That which is claimed is:

1. In a method of culturing avian hemopoietic cells in a culture medium, the improvement comprising:
   including arian embryo extract in said culture medium so that hemopoietic progenitor cells of an earlier ontogenic stage are obtained than those hemopoietic progenitor cells obtained when avian embryo extract is not included in said culture medium, wherein said earlier stage hemopoietic cells are:
   intensely basophilic after May-Grünwald-Giemsa staining; and
   essentially free of hemopoietic differentiation markers for granulocytic colony-forming cells (G-CFC), monocytic colony-forming cells (/M-CFC), and granulocytic/monocyctic colony-forming cells (CM-CFC) after May-Grünwald-Giemsa staining.

2. A method according to claim 1, wherein said culture medium is a semi-solid culture medium.

3. A method according to claim 1, wherein said earlier stage hemopoietic cells are larger in size than G-CFC, M-CGC, or GM-CFC descended from a cell of said arian embryonic hemopoietic organ tissue.

4. A method according to claim 1, wherein said avian hemopoietic progenitor cells are chicken hemopoietic progenitor cells, and wherein said avian embryo extract is chicken embryo extract.

5. A cell culture consisting essentially of isolated early avian hemopoietic progenitor cells, wherein said progenitor cells are:
   descended from an avian embryonic hemopoietic organ tissue cell;
   intensely basophilic after May-Grünwald-Giemsa staining; and
   essentially free of hemopoietic differentiation markers for granulocytic colony-forming cells of (G-CFC), monocytic colony-forming cells (M-CFC), and granulocytic/monocytic colony-forming cells (GM-CFC) after May-Grünwald-Giemsa staining.

6. A cell culture according to claim 5, wherein said progenitor cells are larger in size than G-CFC, M-CGC, or GM-CFC descended from a cell of said arian embryonic hemopoietic organ tissue.

7. A cell culture according to claim 5, further comprising a liquid aqueous medium.

8. A cell culture according to claim 5, further comprising a semi-solid medium.

9. A cell culture according to claim 5, further comprising avian embryo extract.

10. A cell culture according to claim 5, wherein said hemopoietic progenitor cells are selected from the group consisting of chicken, turkey, duck, geese, quail, and pheasant hemopoietic progenitor cells.

11. An isolated early avian hemopoietic progenitor cell, which cell is:
   descended from an avian embryonic hemopoietic organ tissue cell;
   intensely basophilic after May-Grünwald-Giemsa staining; and
   essentially free of hemopoietic differentiation markers for granulocytic colony-forming cells (G-CFC), monocytic colony-forming cells (M-CGC), and granulocytic/monocytic colony-forming cells (GM-CFC) after May-Grünwald-Giemsa staining.

12. An isolated early avian hemopoietic progenitor cell according to claim 11, wherein said cell is larger in size than G-CFC, M-CGC, or GM-CFC descended from a cell of said avian embryonic hemopoietic organ tissue.

13. An isolated early arian hemopoietic progenitor cell according to claim 11, wherein said cell is selected from the group consisting of chicken, turkey, duck, geese, quail, and pheasant hemopoietic progenitor cells.

14. An isolated early arian hemopoietic progenitor cell according to claim 11, wherein said cell is a chicken hemopoietic progenitor cell.

15. A pharmaceutical formulation consisting essentially of early avian hemopoietic progenitor cells, wherein said progenitor cells are:
   descended from an avian embryonic hemopoietic organ tissue cell;
   intensely basophilic after May-Grünwald-Giemsa staining; and
   essentially free of hemopoietic differentiation markers for granulocytic colony-forming cells (G-CFC), monocytic colony-forming cells (M-CFC), and granulocytic/monocytic colony-forming cells (GM-CFC) after May-Grünwald-Giemsa staining.

16. A pharmaceutical formulation according to claim 15 wherein said progenitor cells are larger in size than G-CFC, M-CGC, or GM-CFC descended from a cell of said avian embryonic hemopoietic organ tissue.

17. A pharmaceutical formulation according to claim 15 sealed in a sterile container.

18. A pharmaceutical formulation according to claim 15, further comprising an aqueous pharmaceutically-acceptable carrier.

19. A pharmaceutical formulation according to claim 15, further comprising a growth medium.

20. A pharmaceutical formulation according to claim 15, wherein said hemopoietic progenitor cells are cryopreserved.

* * * * *